(12) United States Patent
Bare et al.

(10) Patent No.: US 8,460,227 B2
(45) Date of Patent: Jun. 11, 2013

(54) CYTOKINE CONCENTRATION SYSTEM

(75) Inventors: Christopher Bare, Naples, FL (US); David O. Shepard, Naples, FL (US)

(73) Assignee: Arthrex, Inc., Naples, FL (US)

( * ) Notice: Subject to any disclaimer, the term of this patent is extended or adjusted under 35 U.S.C. 154(b) by 537 days.

(21) Appl. No.: 12/616,081

(22) Filed: Nov. 10, 2009

(65) Prior Publication Data
US 2010/0125236 A1    May 20, 2010

Related U.S. Application Data

(60) Provisional application No. 61/115,411, filed on Nov. 17, 2008.

(51) Int. Cl.
*A61M 37/00* (2006.01)
*A61B 19/00* (2006.01)

(52) U.S. Cl.
USPC .......................................... 604/6.15; 604/403

(58) Field of Classification Search
USPC ..... 604/403–416, 6.15; 210/787–789; 435/41
See application file for complete search history.

(56) References Cited

U.S. PATENT DOCUMENTS

| | | | |
|---|---|---|---|
| 6,713,246 B1 | 3/2004 | Reinecke et al. | |
| 6,759,188 B2 | 7/2004 | Reinecke et al. | |
| 2002/0185457 A1* | 12/2002 | Smith et al. | 210/787 |
| 2008/0283474 A1* | 11/2008 | Leach et al. | 210/789 |
| 2009/0047242 A1* | 2/2009 | Reinecke et al. | 424/85.2 |
| 2009/0054865 A1* | 2/2009 | Brandenburger et al. | 604/415 |

FOREIGN PATENT DOCUMENTS

| | | | |
|---|---|---|---|
| DE | 10 2006 005 016 A1 * | 1/2006 | |
| DE | 10 2006 005 016 A1 | 8/2007 | |
| WO | WO 2008/127639 A1 | 10/2008 | |

OTHER PUBLICATIONS

William P. Arend and Donald Y. M. Leung, "IgG Induction of IL-1 Recepto Antagonist Production by Human Monocytes", Immunological Reviews, 1994, pp. 70-78.

L. S. Andersen et al., "IgG for Intravenous Use, Autologous Serum and Plasma Induce Comparable Interleukin-1 Receptor Antagonist Liberation From Human Mononuclear Cells: An In Vitro Phenomenon Depending Upon Plastic Adherence", Autoimmunity, 1995, vol. 22, pp. 127-133.

* cited by examiner

*Primary Examiner* — Philip R Wiest
(74) *Attorney, Agent, or Firm* — Dickstein Shapiro LLP

(57) ABSTRACT

Apparatus and methods for producing interleukin-1 receptor antagonist and/or other prophylatically or therapeutically effective protein. Blood is obtained from a patient with a conventional syringe and then introduced into dual luer lock centrifuge tube. The dual luer lock centrifuge tube is provided with beads that are coated with a silanized coating. The container is then incubated and centrifuged. Subsequent to the incubation and the centrifugation, the serum containing autologous therapeutically active protein, such as IL-1Ra, in the container is withdrawn through the luer lock of the container, and injected back into the patient.

10 Claims, 5 Drawing Sheets

Baseline, IRAP, and IRAP II levels of TNF-$\alpha$, IL-10, and IL-1$\beta$
(* denotes significant difference)

Baseline, IRAP, and IRAP II levels of IL-1ra
(* denotes significant difference)

IRAP, and IRAP II IL-1ra/ IL-1$\beta$ ratios
(* denotes significant difference)

CYTOKINE CONCENTRATION SYSTEM

CROSS-REFERENCE TO RELATED APPLICATIONS

This application claims the benefit of U.S. Provisional Application No. 61/115,411, filed Nov. 17, 2008, the entire disclosure of which is incorporated by reference herein.

FIELD OF THE INVENTION

The present invention relates to methods and apparatus for producing therapeutically active proteins, such as anti-inflammatory cytokines.

BACKGROUND OF THE INVENTION

Interleukin-1 (IL-1) plays a key role in the pathology of osteoarthritis or intervertebral disc degeneration/prolapse. The biological antagonist, interleukin-1 receptor antagonist (IL-1Ra), intervenes in the physiological mechanism of these diseases. IL-1Ra is a naturally occurring, structural derivative of IL-1 that competitively binds to the receptor and inhibits the biological effects of IL-1. The endogenous effects of IL-1ra are anti-inflammatory in nature, opposite to that of IL-1. A minimum IL-1ra/IL-1β ratio of 10:1 is required to inhibit IL-1 activity.

It has been known for some years that IL-1Ra can be synthesized by recombinant methods. However, autologous IL-1Ra, like all autologous proteins that are intrinsic to the body, is advantageous because the natural post-translational modifications such as glycosylations are already present. This is not the case with recombinant proteins because they are produced in prokaryotic hosts.

Stimulation of monocytes by adherent immunoglobulin G to form the interleukin-1 receptor antagonist is described by Arend and Leung in Immunological Reviews (1994) 139, 71-78 and Moore et al. in Am. J. Respir. Cell Mol. Biol. (1992) 6, 569-575. Andersen et al. in Autoimmunity (1995) 22, 127-133 explains that the therapeutic effect of immunoglobulin G to be observed in vivo cannot be attributed to an enhanced formation of interleukin-1 receptor antagonist, and that the in vitro formation of the interleukin-1 receptor antagonist (IL-1Ra) by monocytes depends on serum and plasma constituents adsorbed on polypropylene. The therapeutic use of adsorbed serum and plasma constituents to stimulate the formation of therapeutically interesting proteins in therapies is not only very costly but also involves the risk of contamination with infectious particles with which the serum and plasma constituents may be contaminated.

U.S. Pat. Nos. 6,713,246 and 6,759,188 to Reinecke disclose a method for producing IL-1Ra which can be employed directly in the therapy without using adsorbed serum and plasma constituents. Specifically, Reinecke provides a method for producing IL-1Ra in a special syringe made of glass, quartz or a plastic, the syringe being filled with blood, and incubated, to form the IL-1Ra being formed. The internal structure of the Reinecke syringe consists of a special material, in particular a glass, plastic, quartz and/or corundum, the surface of which is modified with the aid of a corrosive agent (chromosulphonic acid). The syringe is filled with a patient's blood and incubated to form IL-1Ra. The blood enriched with the protein is then centrifuged (to remove solid constituents such as blood platelets) and the serum containing IL-1Ra is reinjected into the patient (for example, into a diseased joint of the patient).

The syringe used by Reinecke has its inner surface textured by the acid and further includes glass beads to increase the internal surface area of the syringe and, thus, to provide a larger inducing surface. The glass beads, with a diameter of from 1 to 5 mm, occupy no more than 50% of the internal volume of the syringe. In Reinecke's method, the syringe is used to remove the patient's blood, to process the blood (to produce IL-1Ra), and then reinject the autologous IL-1Ra back into the patient. The present invention expands upon this method, to produce autologous IL-1Ra in a more efficient manner.

SUMMARY OF THE INVENTION

The present invention provides apparatus and methods for producing anti-inflammatory cytokines, specifically IL-1Ra, and/or other therapeutically active proteins, for treatment of human or non-human damaged tissue such as cartilage and neurological tissue. Blood is withdrawn from the patient and then transferred into a special container provided with a cap configured to allow the patient's blood to flow on an inner side of the container, to prevent lyses of the blood cells. The container is a dual luer lock centrifuge tube that contains beads that are coated with a silanized coating. The container is then incubated and centrifuged. Subsequent to the incubation and the centrifugation, the serum containing the autologous therapeutically active protein (e.g., IL-1Ra) in the container is withdrawn through the luer lock of the container, and injected back into the patient.

The present invention also provides a method of obtaining anti-inflammatory cytokines for treatment of connective tissue injuries. The method comprises the steps of: (i) providing an apparatus comprising a dual luer lock centrifuge tube with beads; (ii) drawing blood into another container; (iii) injecting the blood from the another container into the dual luer lock centrifuge tube; (iv) incubating and centrifuging the blood in the beads/dual luer lock centrifuge tube; and (iv) removing, through the luer lock of the beads/dual luer lock centrifuge tube, serum containing the IL-1Ra or other protein generated during incubation, and injecting that protein back into the patient.

Other features and advantages of the present invention will become apparent from the following description of the invention, which refers to the accompanying drawing.

DETAILED DESCRIPTION OF THE PREFERRED EMBODIMENTS

Figure 1:
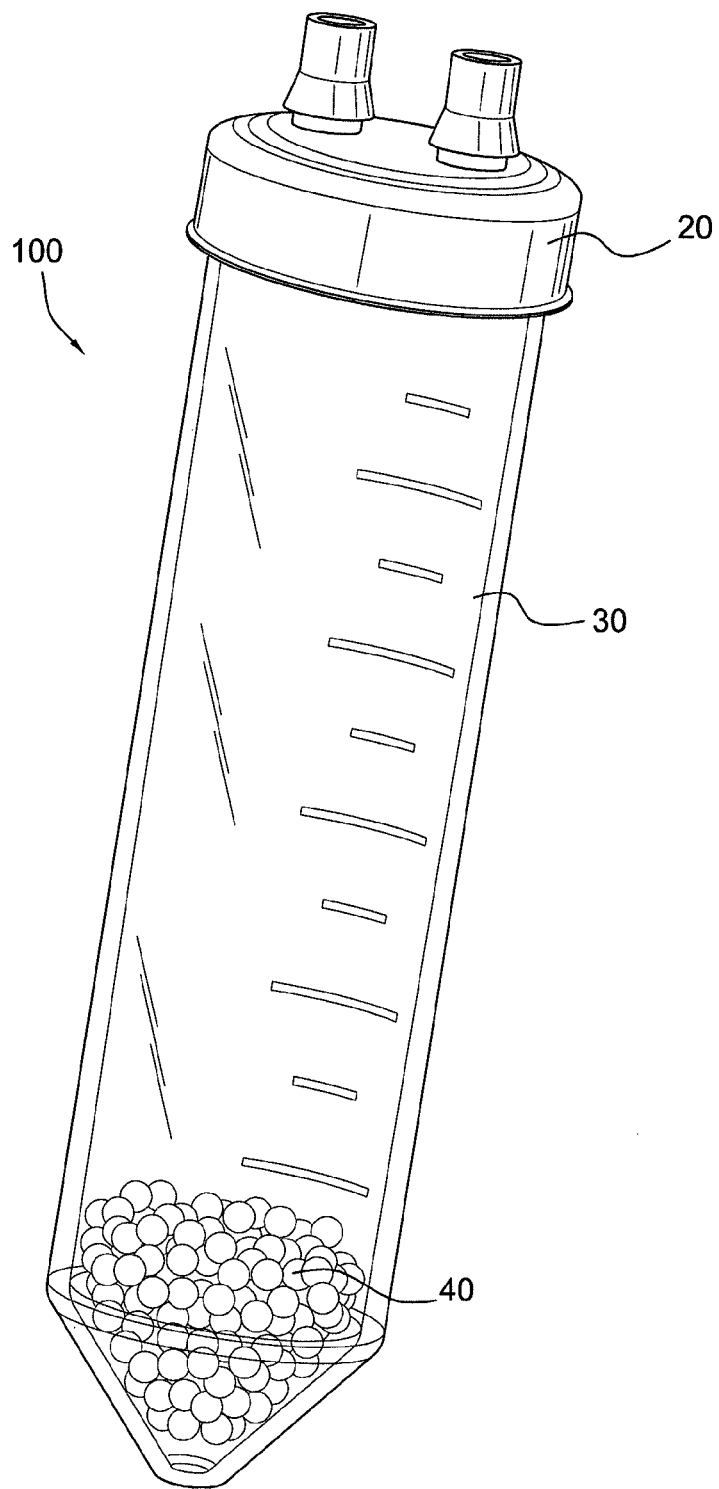
FIG. 1 illustrates a perspective view of a beads/dual luer lock centrifuge tube of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides apparatus and methods for providing anti-inflammatory cytokines, specifically IL-1Ra, or other beneficial protein, for treatment of human or non-human damaged tissue such as cartilage and musculoskeletal tissue.

Blood is withdrawn from the patient and then transferred into a special container with a cap that is configured to allow the patient's blood to flow on an inner side of the container, to prevent lyses of the blood cells. The container is a dual luer lock centrifuge tube that contains beads that are coated with a silanized coating. The container is then incubated and centrifuged. Subsequent to the incubation and the centrifugation, the serum containing autologous IL- is withdrawn through the luer lock of the container, and injected back into the patient.

According to an exemplary embodiment, blood is withdrawn from the patient using a two-container system comprising a first container (for example, a conventional syringe) and a second container (for example, a dual luer lock centrifuge tube). Approximately 50 ml of blood is withdrawn with the first container and then transferred into the second container (the dual luer lock centrifuge tube). The second container comprises a cap that is configured to allow the patient's blood to flow on an inner side of the second container, to prevent lyses of the blood cells. The dual luer lock centrifuge tube contains beads which are not etched with chromium sulfate, as in Reinecke, but rather are coated with a silanized coating. The second container is then incubated and centrifuged. Subsequent to the incubation and the centrifugation, the serum containing autologous IL-1Ra is withdrawn through the luer lock of the second container, and injected back into the patient.

The present invention also provides a method of obtaining anti-inflammatory cytokines for treatment of tissue injuries. The method comprises the steps of: (i) providing an apparatus comprising a dual luer lock centrifuge tube with beads; (ii) drawing blood into a conventional syringe; (iii) injecting the blood from the conventional syringe into the dual luer lock centrifuge tube; (iv) incubating and centrifuging the blood in the beads/dual luer lock centrifuge tube; and (iv) removing, through the luer lock of the beads/dual luer lock centrifuge tube, serum containing the IL-1Ra protein generated during incubation, and injecting that protein back into the patient.

According to an exemplary embodiment, blood is first obtained from a patient with a conventional syringe. The blood is then introduced into the beads/dual luer lock centrifuge tube through a conduit that forms an angle with the longitudinal axis of the tube, to allow the blood to flow into the tube on the sidewall of the tube, to prevent lyses of the blood cells. The blood is subsequently incubated at 37° C., to stimulate the monocytes in the blood to produce IL-1Ra. The blood containing elevated levels of IL-1Ra is then centrifuged in the beads/dual luer lock centrifuge tube to isolate the IL-1Ra protein. The serum containing the concentrated IL-1Ra protein is removed through a luer lock of the beads/dual luer lock centrifuge tube. The isolated protein may be subsequently employed in surgical repairs, promoting the healing of the repair in orthopedic and neurological applications, for example.

Referring now to the drawings, where like elements are designated by like reference numerals, FIGS. 1-4 illustrate an exemplary embodiment of a dual luer lock centrifuge tube 100 of the present invention. Tube 100 includes a cap 20 securely attached to container 30 containing beads 40. The tube 100 and cap 20 provide for a closed system allowing for sterile incubation and withdrawal of the serum containing IL-1Ra.

Figure 2:
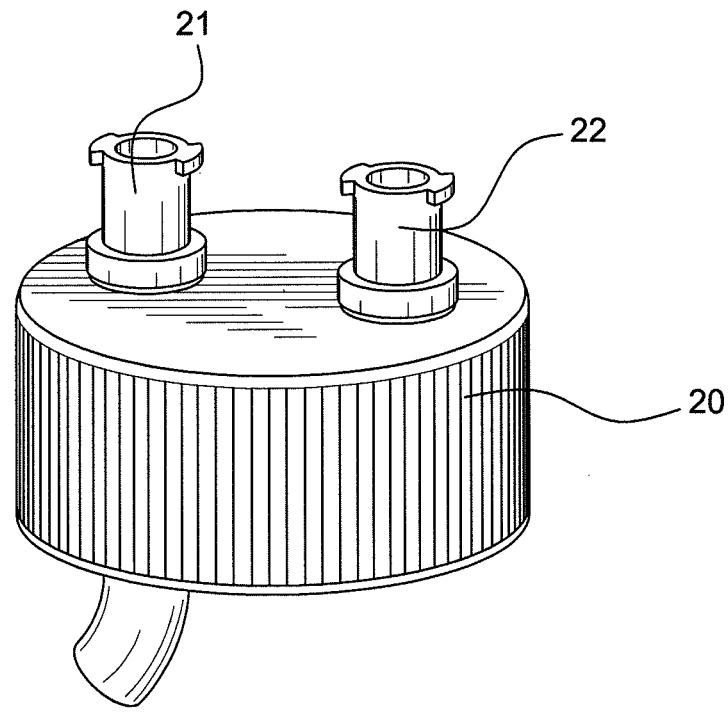
FIGS. 2-4 illustrate various views of the cap of the beads/dual luer lock centrifuge tube of the present invention.
Figure 3:
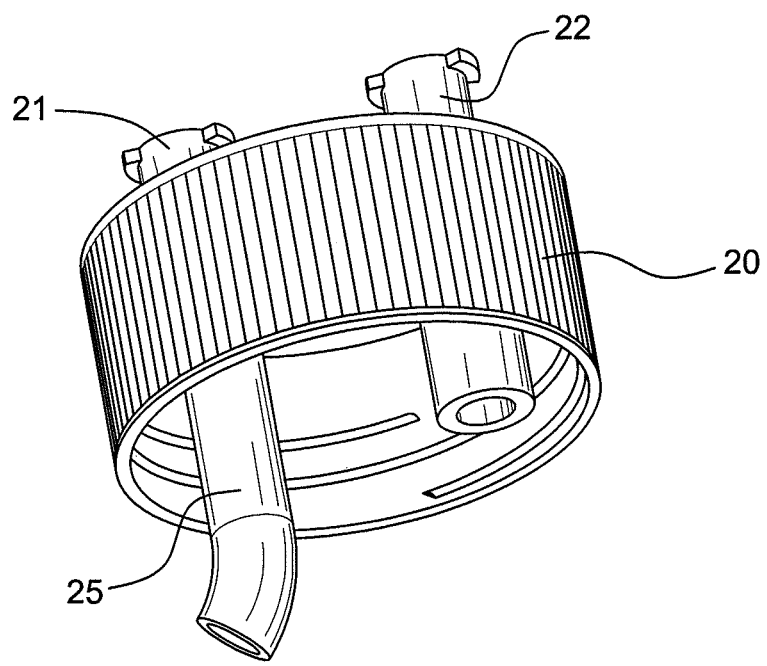
Figure 4:
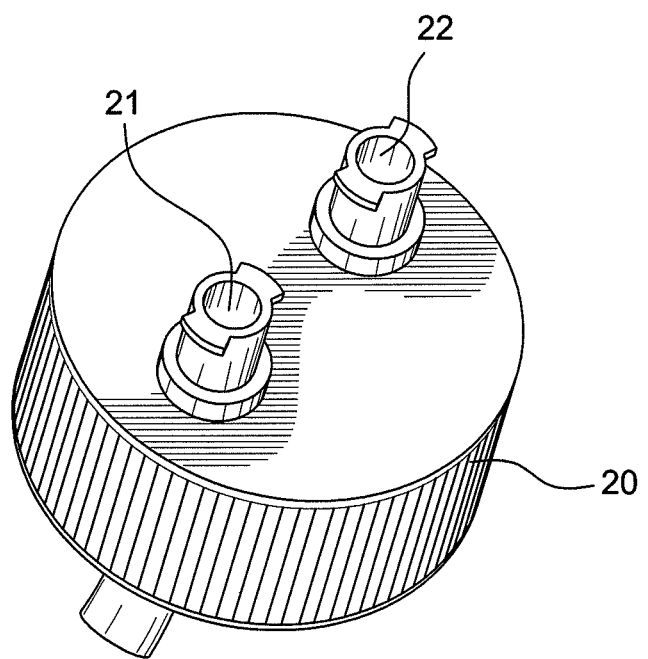

Details of the cap 20 of the dual luer lock centrifuge tube 100 of the present invention are illustrated in FIGS. 2-4. Cap 20 comprises luer locks 21, 22, at least one of the luer locks including a conduit 25 with a distal end having an angular orientation (i.e., at least a portion of the conduit 25 forms an angle with the longitudinal axis of container 30, as shown in FIG. 3). The angular orientation allows blood (withdrawn from a patient with an ordinary syringe) to be introduced into the container 30 by flowing on the side (the inner side) of the container 30, to prevent lyses of the blood cells. The angular orientation may be between 45-180 degrees. Alternately, the end of the conduit may be shaped or offset from the axis of the conduit.

The container 30 has a conical shape and a closed distal end for placement in a centrifuge. The container is made from a sterilizable material such as polypropylene and holds a volume of approximately 60 ml although it could be any size that would fit within a centrifuge. The outside of the container has incremental markings to assist in withdrawing the serum in the desired dosing quantities.

The container 30 contains beads 40. The beads are manufactured from a glass like composition such as, borosilicate glass, alumina, silicate, quartz, bioglass, ceramic glass, flint glass, fluorosilicate glass, phosphosilicate glass, and cobalt glass or conundrum. In a preferred embodiment the beads have a spherical shape to provide for a maximum surface area for blood contact. In an alternate embodiment the container may contain gels, wool, powder, plastic, granules or fibers. The beads are provided with a coating to maximize the production of IL-1Ra by the monocytes within the blood. The coating may be silane, surfactants, polyether, polyester, polyurethane, or polyol groups. The beads may range in size from 1-5 mm, but preferably are 3.0 mm. Optimal production of IL-1Ra occurs when the maximum surface area of the beads is exposed to the blood within the container. A maximum amount of blood in the container is also necessary to optimize the production of IL-1Ra. In order to accomplish both goals, the volume of the beads must be minimized to accomplish the maximum exposed surface area. Accordingly, the diameter of the beads has been tailored to maximize the volume of injected blood in the container and maximize the surface area for blood/bead contact.

A method of obtaining concentrated IL-1Ra according to an exemplary embodiment of the present invention will be described below.

Using aseptic technique, prepare the jugular vein for needle penetration. Attach the needle to the 60 mL syringe and puncture the jugular vein.

Harvest ~50 mL of whole blood into the 60 mL syringe.

Remove needle from jugular and detach from syringe.

Unscrew the red tethered cap and loosen the white tethered cap on the centrifuge tube.

Attach the syringe with blood to the red luer and inject blood into the centrifuge tube, holding the syringe and centrifuge tube at an angle of approximate ~60°. The blood should flow against the side of the centrifuge tube. (Take care not to inject above Max Fill Line marked on the centrifuge tube.)

Remove syringe, recap and tighten both tethered male caps, and gently rock the blood in the centrifuge tube.

Place in incubator for approximately 24 hours at 37° C., not to exceed 24 hours.

After incubation, place the centrifuge tube into a centrifuge for 10 minutes at 4000 rpm. Make sure to balance centrifuge with an appropriate counter weight.

Remove white tethered cap and loosen red cap. Slowly draw the serum into a 20 mL syringe using a spinal needle, being careful not to pull up red blood cells.

Attach a sterile 0.22 µm filter between the 20 mL syringe containing the serum and an empty, sterile 6 mL syringe. Transfer 4 mL of serum to the 6 mL syringe, detach the 6 mL syringe and cap.

Repeat until all the serum has been transferred through the sterile filter into the 6 mL syringes. Individual doses may be used immediately or frozen at or less than −18° C. for administration at a later date.

Excess blood and/or serum should be disposed of appropriately.

A method of obtaining concentrated IL-1Ra according to an exemplary embodiment of the present invention will be described below with reference to a particular and only exemplary study and as detailed below:

The objective of the study was two fold: (1) to fabricate a borosilicate bead/tube assembly 100 (IRAP II) of the present invention that performed better than the currently-known IRAP syringe system (IRAP); and (2) to determine the levels of two pro-inflammatory cytokines (IL-1β and TNF-a) and two anti-inflammatory cytokines (IL-1ra and IL-10) in human whole blood using the conventional IRAP syringe and IRAP II centrifuge tube. Biological testing was performed by utilizing enzyme-linked immunosorbant assays (ELISA) to measure serum levels of the cytokines.

Materials and Methods:

IRAP Bead Composition: Beads from a sterilized IRAP syringe were examined using IRF, X-ray Fluorescense Spectroscopy, to determine the elemental composition of the beads.

IRAP Bead SEM: Beads from a sterlized IRAP syringe were sent for SEM analysis.

Blood incubation and ELISA: Blood samples were collected from n=8 healthy volunteers, all male, ages 28-52 with a mean age of 38. Donors were divided into 3 groups: Group A Baseline, 2×10 mL glass vacutainers (Becton Dickinson, Franklin Lakes, N.J.), Group B, a 60 mL IRAP syringe (Orthogen, Düsseldorf, Germany), and Group C, a 50 mL centrifuge tube with silanized borosilicate beads. Approximately 20 mL of blood was collected for Group A, 50 mL of blood was collected for Group B into the large IRAP syringe, and approximately 40 mL of blood was collected for Group C into the polypropylene centrifuge tube. All groups were inverted ten times following collection and the Group B IRAP syringe and Group C IRAP II centrifuge tube were placed into incubator at 37° C. for 24 hours.

The blood samples were spun down in a centrifuge (such as Hermle Z300 centrifuge from Labnet, Edison, N.J.) at about 4000 rpm for about 10 minutes. Group A was centrifuged approximately 15 minutes after it had been drawn (to give the sample time to clot), and groups B and C were centrifuged following a 24 hour incubation period in an incubator (such as 2.5 ft³ Precision Economy Incubator from Precision Scientific, Winchester Va.) at about 37° C. After centrifugation, each donor's serum was removed from the container using a 5 mL polypropylene syringe (Becton Dickinson, Franklin, N.J.) and an 18 gage needle. The serum from each sample was then filtered with 0.22 µm Millex GP filters (Millipore, Billerica, Mass.) aliquotted into 5.0 mL cyrovials (Wheaton, Millville, N.J.), and stored at approximately −81° C.

Serum samples were thawed to room temperature and then tested according to the Quantikine ELISA kit protocols (R&D Systems, Minneapolis, Minn.). The plate wells were washed using a Bio-Tek ELx 50 microplate strip washer, and absorbance of each sample was determined using a Bio-Tek ELx808 absorbance microplate reader. The serum samples for each donor were run in duplicate. Concentrations were calculated using, for example, a KC Junior (Bio-Tek Instruments, Winooski, Vt.), by converting absorbance to concentration based on a standard curve of optical density versus concentration.

Results

XRF: XRF (X-ray Fluorescence Spectroscopy) was performed on the Group B IRAP beads. The results are presented in Table 1 below. The elemental breakdown very closely resembles borosilicate glass ($SiO_2$~81%, $B_2O_3$=~13, $Na_2O$=~4%, and other=~2%).

TABLE 1

XRF analysis of the IRAP beads

| Elemental Compound | % composition |
|---|---|
| SiO2 | 79.73 |
| B2O3 | 12.57 |
| Al2O3 | 3.53 |
| Na2O | 2.94 |
| K2O | 0.71 |
| SO3 | 0.169 |
| TiO2 | 0.1612 |
| Cl | 0.0609 |
| Fe2O3 | 0.0465 |
| SrO | 0.0354 |
| BaO | 0.0353 |
| NiO | 0.0076 |
| ZnO | 0.007 |
| PB | 0.000032 |

Figure 5:
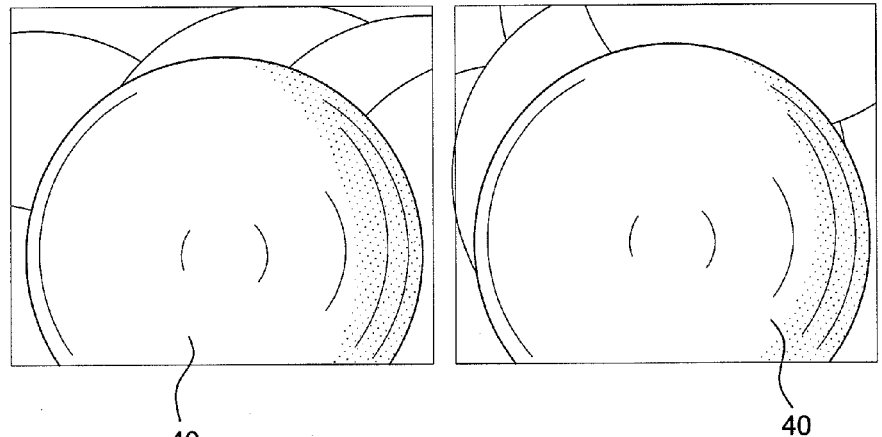
FIG. 5 illustrates a magnified view of IRAP 3.5 mm beads (25× Magnification).

SEM: SEM analysis was performed to determine if the Group B IRAP beads were etched with 50% (volume/volume) $CrSO_4$ as described in the Meijer paper (FIG. 5) (Meijer, H., et al., *The production of anti-inflammatory cytokines in whole blood by physico-chemical induction.* Inflamm Res, 2003. 52(10): p. 404-7). Micro-craters were noticed on the surface of the IRAP borosilicate beads. It was inconclusive whether these were created by the CrSO4 or if this was a product of the beads colliding against each other within the syringe. FIG. 5 illustrates a view of Group B IRAP 3.5 mm beads (25× Magnification).

Bead Calculation: In order to match the surface area created by the Group B IRAP beads (d=3.5 mm), the Group C TRAP II centrifuge tubes of the present invention were loaded with enough silanized beads (d=3.0 mm) to match the total surface area created by all the beads in the Group B IRAP syringe. In the original Orthogen paper (Meijer et al., *The production of anti-inflammatory cytokines in whole blood by physico-chemical induction.* Inflamm Res, 2003. 52(10): p. 404-7), the syringe contained 200 glass beads with a diameter of 2.5 mm, creating a total surface area of 39.27 cm², Equation 1 below.

Equation 1: Total surface area of the glass beads ($SA_1$) was determined using the formula of a sphere multiplied by the number of beads ($n_1$).

$$SA_1 = 4\pi r_1^2 n_1$$

$$SA_1 = 4\pi \left(\frac{0.25 \text{ cm}}{2}\right)^2 \times 200 = 39.27 \text{ cm}^2$$

There were n=240 glass beads in the current 60 mL IRAP syringe supplied by Orthogen, and the measured bead diameter was 3.5 mm (contradicting the Orthogen paper). The total surface area of glass beads was 92.4 cm$_2$, Equation 2 below.

Equation 2: IRAP measured surface area of the glass beads ($SA_2$) was determined using the formula of a sphere multiplied by the number of beads ($N_2$).

$$SA_2 = (4\pi r_2^2) \times n_2$$

$$SA_2 = 4\pi \left(\frac{0.35 \text{ cm}}{2}\right)^2 \times 240 = 92.4 \text{ cm}^2$$

The number of beads ($n_0$) required to equal the surface area created by all the beads in the Group B IRAP syringe was calculated using Equation 3 below.

Equation 3: The number of 3.0 mm beads ($n_0$) for the Group C centrifuge tube needed to equal the surface area of the Group B IRAP syringe is calculated by setting the total surface area equal to $SA_2$ and solving for $n_0$.

$$SA_1 = 4\pi r_2^2 n_0$$

$$92.4 \text{ cm}^2 = 4\pi \left(\frac{0.30 \text{ cm}}{2}\right)^2 \times n_0$$

$$n_0 \approx 327 \text{ beads}$$

Each Group C IRAP II polypropylene centrifuge tube was loaded with 327 silanized borosilicate glass beads, d=3.0 mm.

Results

Figure 6:
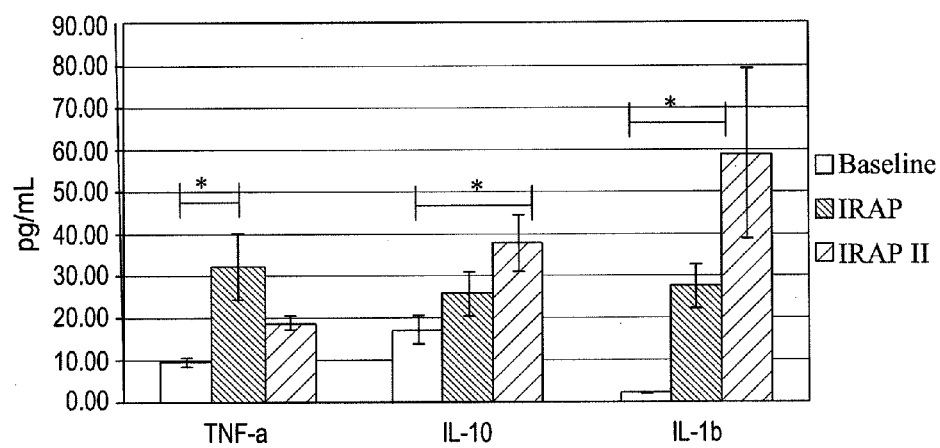
FIG. 6 illustrates Baseline, IRAP, and IRAP II levels of TNF-a, IL-10, and IL-1β.
Figure 7:
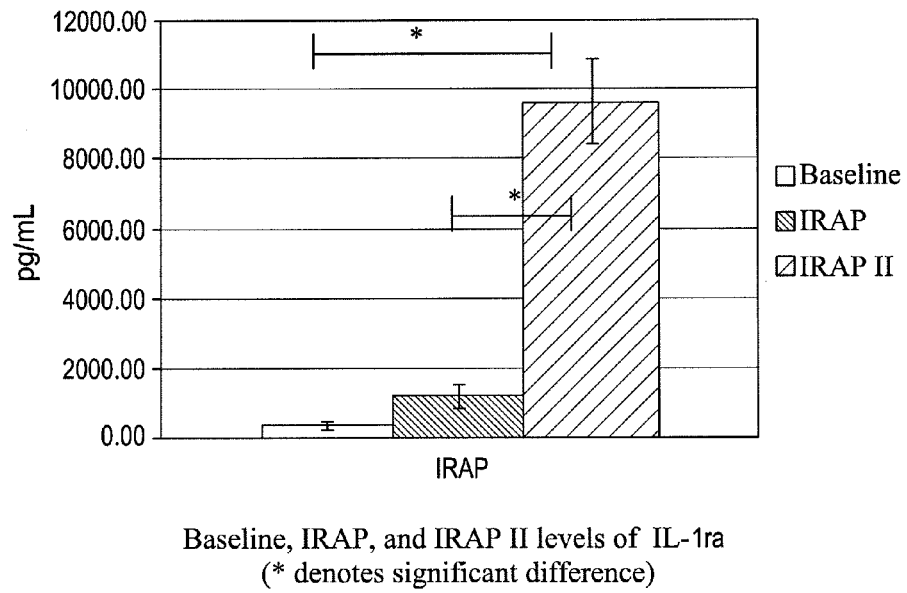
FIG. 7 illustrates Baseline, IRAP, and IRAP II levels of IL-1ra.

ELISA: The mean values, range, and standard error of n=8 donors were calculated for TNF-a, IL-10, IL-1β, and IL-1ra, Table 2 below. FIG. 6 and FIG. 7 depict all cytokine mean levels. Standard error is utilized to compare the past studies.

TNF-a: IRAP II levels were not significantly different compared to IRAP and baseline (p=0.176 and p=0.551, respectively). Higher levels associated with IRAP were significantly different than baseline levels (p=0.009).

IL-10: Higher levels in IRAP II were significantly different than baseline levels (p=0.031). IRAP II was not significantly different than IRAP (p=0.349, p<0.05), and IRAP was not significantly different from baseline levels (p=0.750, p>0.05).

IL-1β: Higher levels in IRAP II were significantly different than baseline levels (p=0.009). IRAP II was not significantly different from baseline levels (p=0.239, P<0.05), and IRAP was not significantly different from baseline levels (p=0.431, P>0.05).

IL-1ra: Higher levels in IRAP II were significantly different compared to both baseline levels (p<0.001) and IRAP levels (p<0.001). IRAP was not significantly different from baseline levels (p=1.000, P>0.001).

TABLE 2

The mean of n = 8 donors is shown with the range and the standard error (STE).

| | TNF-alpha (pg/ml): pro-inflammatory | | | | IL-10 (pg/ml): anti-inflammatory | | |
|---|---|---|---|---|---|---|---|
| | Means | Range | StErr | | Mean | Range | StErr |
| Baseline | 9.5 | 6.1-14.5 | 1.6 | Baseline | 16.9 | 9.7-38.5 | 0.1 |
| IRAP | 32.3 | 13.8-74.5 | 8.0 | IRAP | 25.7 | 16.0-57.5 | 5.4 |
| IRAP II | 18.8 | 10.1-23.5 | 1.7 | IRAP II | 37.8 | 22.7-68.0 | 20.1 |

| | IL-1beta (pg/ml): pro-inflammatory | | | | IL-ra (pg/ml): anti-inflammatory | | |
|---|---|---|---|---|---|---|---|
| | Mean | Range | StErr | | Mean | Range | StErr |
| Baseline | <3.9 | <3.9 | <3.9 | Baseline | 355 | 118-1113 | 115 |
| IRAP | 27.5 | 9.3-50.4 | 54 | IRAP | 1233 | 261-2708 | 344 |
| IRAP II | 58.8 | 23.9-195.2 | 20.1 | IRAP II | 9688 | 5908-14604 | 1196 |

Values denoted with a less than symbol indicate for factor was below the limit of detection of the assay kit.

FIG. 6 illustrates Baseline, IRAP, and IRAP II levels of TNF-a, IL-10, and IL-1β (*denotes significant difference). FIG. 7 illustrates Baseline, IRAP, and IRAP II levels of IL-1ra (*denotes significant difference).

A minimum IL-1ra/IL-1β ratio of 10:1 is required to inhibit IL-1 activity [2]. IL-1ra/IL-1β ratios are illustrated in FIG. 4 and Table 3. A test (a=0.05) was performed and the higher ratio produced by IRAP II is significantly different than IRAP (p=0.002).

Figure 8:
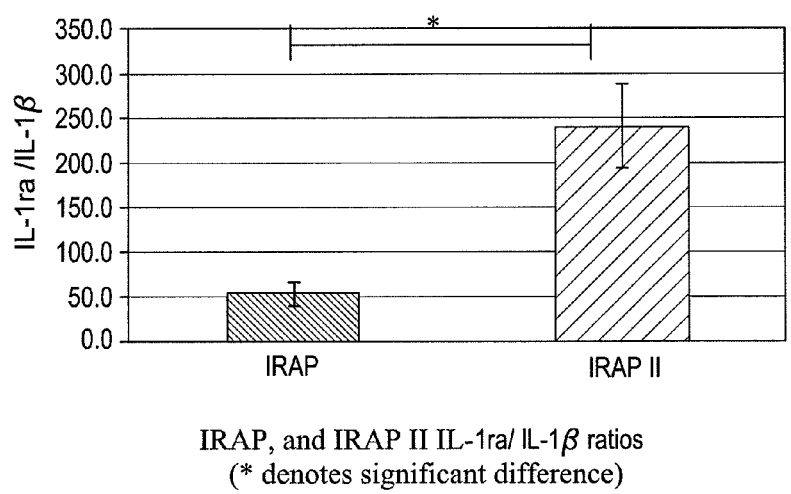
FIG. 8 illustrates IRAP and IRAP II IL-1ra/IL-1β ratios.

FIG. 8 illustrates IRAP and IRAP II IL-1ra/IL-1β ratios (*denotes significant difference).

TABLE 3

The IL-1ra/IL-1β mean, range, and standard error (STE) of n = 8 donors

| | Ratio of IL-ra/IL-1beta | | |
|---|---|---|---|
| | Mean | Range | StErr |
| IRAP | 53.1 | 10.4-134.5 | 16.0 |
| IRAP II | 239.6 | 60.7-461.2 | 46.8 |

Discussion

In comparison to the Group B system, Group C offers a more convenient two-container system which significantly increases the amount of autologous IL-1ra produced. Other distinguishing differences include the contained silanized borosilicate spheres, a specific sphere diameter which not only maximizes the sphere surface area/blood contact, but also maximizes the amount of blood volume in the Group C centrifuge tube. Research also indicated that the autologous serum produced by Group C centrifuge tube contains a higher ratio of anti-inflammatory proteins (IL-1ra) to pro-inflammatory proteins (IL-1). Since the serum produced by Group C contains a concentrated combination of biologically relevant autologous growth factors, it can be an attractive option in treatment for tissue injury or osteoarthritis.

Conclusion

In vitro incubation of human whole blood at body temperature for 24 hours using the Group C IRAP II centrifuge system induces production of anti- and pro-inflammatory cytokines. IL-10, IL-1β and TNF-a levels in the Group C IRAP II system were not different compared to the Group B IRAP. The Group C IRAP II produces higher levels of IL-1ra when compared to the Group B IRAP. The higher levels of IL-1ra also led to a higher ratio of IL-1ra/IL-1β.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method for producing a therapeutically active protein in a two-container system, comprising:
    withdrawing blood from a mammal into a first container of the two-container system;
    injecting the blood from the first container into a second container of the two-container system, wherein the second container is a dual port centrifuge tube, the second container defining a longitudinal axis and comprising a cap having dual ports, a first port for injecting blood into the second container and a second port for removing serum from the second container, the second container containing beads or spheres, and wherein the blood is injected from the first container into the centrifuge tube through the first port of the dual port centrifuge tube; and
    incubating the dual port centrifuge tube for a sufficient time and at a sufficient temperature to produce a therapeutically active protein in the blood;
    centrifuging the dual port centrifuge tube to form a serum containing the therapeutically active protein;
    removing the serum from the dual port centrifuge tube through the second port of the dual the dual port centrifuge tube, wherein the serum contains the therapeutically active protein.

2. The method of claim 1, wherein the therapeutically active protein is IL-1Ra and the method further comprising the step of removing the produced IL-1Ra in the blood through a luer lock of the second container, and injecting back the produced IL-1Ra into the mammal to promote tissue repair.

3. The method of claim 1, wherein the step of injecting the blood into the second container further comprises introducing the blood through a conduit of the second container, the conduit forming an angle with a longitudinal axis of the second container, to allow the blood to flow into the second container and on a sidewall of the second container.

4. The method of claim 1, wherein the first container is a syringe.

5. The method of claim 1, wherein the second container is a dual luer lock centrifuge tube.

6. The method of claim 1, wherein the second container comprises beads, spheres, gels, wool, powder, granules, fibers or particles made of glass, plastic, corundum and/or quartz in the second container.

7. The method of claim 1, wherein the second container comprises particles coated with a silanized coating.

8. The method according to claim 1, wherein the blood is incubated in the second container from about 12 to 72 hours.

9. The method according to claim 1, wherein the blood is incubated in the second container at about 20 to 37° C.

10. The method according to claim 1, wherein the therapeutically active protein is IL-1Ra.

* * * * *